(12) United States Patent
Botea et al.

(10) Patent No.: US 10,430,395 B2
(45) Date of Patent: Oct. 1, 2019

(54) ITERATIVE WIDENING SEARCH FOR DESIGNING CHEMICAL COMPOUNDS

(71) Applicant: International Business Machines Corporation, Armonk, NY (US)

(72) Inventors: Adi Ionel Botea, Dublin (IE); Beat Buesser, Dublin (IE); Bei Chen, Dublin (IE); Akihiro Kishimoto, Dublin (IE)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 189 days.

(21) Appl. No.: 15/446,786

(22) Filed: Mar. 1, 2017

(65) Prior Publication Data
US 2018/0253453 A1 Sep. 6, 2018

(51) Int. Cl.
*G06F 16/00* (2019.01)
*G06F 16/21* (2019.01)
(Continued)

(52) U.S. Cl.
CPC ........ *G06F 16/217* (2019.01); *G06F 16/2455* (2019.01); *G16C 20/40* (2019.02); *G16C 20/50* (2019.02); *G16C 20/70* (2019.02)

(58) Field of Classification Search
CPC ......... G06F 17/30306; G06F 17/30477; G06F 19/705; G06F 19/707; G06F 17/30979; G06F 17/30929; G06F 17/30657; G06F 17/30424; G06F 16/217; G06F 16/2455; G06F 16/245; G06F 16/3331;
(Continued)

(56) References Cited

U.S. PATENT DOCUMENTS

| 4,747,059 A * | 5/1988 | Hirayama ............... G16C 20/70 703/12 |
| 6,421,612 B1 | 7/2002 | Agrafiotis et al. |

(Continued)

FOREIGN PATENT DOCUMENTS

| CN | 106023121 A | 10/2016 |
| EP | 2581849 A1 | 4/2013 |

(Continued)

OTHER PUBLICATIONS

Cazenave, "Iterative Widening", 2001, 6 pages.
(Continued)

*Primary Examiner* — Noosha Arjomandi
(74) *Attorney, Agent, or Firm* — Amin, Turocy & Watson, LLP

(57) ABSTRACT

Techniques facilitating iterative widening search for designing chemical compounds are provided. A computer-implemented method can comprise receiving, by a system operatively coupled to a processor, an indication of a constrained structure portion of a chemical compound and a first unconstrained structure portion of the chemical compound. The method can also comprise determining, by the system, a second unconstrained structure portion for the chemical compound based on a determination that the second unconstrained structure portion satisfies a defined condition related to a difference between the first unconstrained structure portion and the second unconstrained structure portion.

9 Claims, 10 Drawing Sheets

(51) Int. Cl.
*G06F 16/2455* (2019.01)
*G16C 20/40* (2019.01)
*G16C 20/50* (2019.01)
*G16C 20/70* (2019.01)

(58) Field of Classification Search
CPC . G06F 16/835; G06F 16/90335; G16C 20/40; G16C 20/50; G16C 20/70
See application file for complete search history.

(56) References Cited

U.S. PATENT DOCUMENTS

| | | | |
|---|---|---|---|
| 6,434,490 | B1 | 8/2002 | Agrafiotis et al. |
| 6,721,754 | B1* | 4/2004 | Hurst ............... G16C 20/40 707/714 |
| 7,704,699 | B2 | 4/2010 | Sproch et al. |
| 7,801,685 | B2 | 9/2010 | Ho |
| 8,036,867 | B2 | 10/2011 | Prakash et al. |
| 2002/0049548 | A1 | 4/2002 | Bunin |
| 2004/0117164 | A1 | 6/2004 | Elling et al. |
| 2005/0266575 | A1* | 12/2005 | Mayo ............... C07K 7/08 436/86 |
| 2007/0276851 | A1* | 11/2007 | Friedlander ........ G06F 16/283 |
| 2008/0177770 | A1* | 7/2008 | Friedlander ........ G06F 21/6227 |
| 2010/0305929 | A1 | 12/2010 | Andersen et al. |
| 2011/0060437 | A1* | 3/2011 | Durham, III ...... G06F 16/58 700/97 |
| 2012/0084299 | A1* | 4/2012 | Cai ................... G06F 19/705 707/748 |
| 2012/0164631 | A1 | 6/2012 | Turner et al. |
| 2014/0171332 | A1 | 6/2014 | Katz et al. |
| 2015/0142730 | A1* | 5/2015 | Dakshanamurthy ................... G06F 19/324 707/609 |
| 2018/0137125 | A1* | 5/2018 | Vittorio ............. G06Q 50/10 |

FOREIGN PATENT DOCUMENTS

| | | |
|---|---|---|
| WO | 2008025571 A2 | 3/2008 |
| WO | 2011061548 A2 | 5/2011 |

OTHER PUBLICATIONS

Harvey et al.,"Limited Discrepancy Search", 1990, 7 pages.
Thomsen, "Lambda-Search in Game Trees—With application to Go", Computers and Games, 2000, Springer, 20 pages.
Lavecchia, "Machine-Learning Approaches in Drug Discovery: Methods and Applications", Drug Discovery Today, Nov. 2014, Elsevier Ltd.,14 pages.
Abt et al.,"A Sequential Approach for Identifying Lead Compounds in Large Chemical Database", Statistical Science, May 2001, pp. 154-168, vol. 16, No. 2, Institute of Mathematical Statistics, 16 pages.
"SciFinder—A CAS Solution", CAS—A Division of the American Chemical Society, 1 page. Retrieved on Feb. 2, 2017. http://www.cas.org/products/scifinder.
"Reaxys: The Shortest Path to Chemistry Research Answers", Elsevier, 9 pages. Retrieved on Feb. 2, 2017. https://www.reaxys.com/.
"ChemInform (CIRX)", 2013, Wiley Information Services GmbH, 1 page. Retrieved on Feb. 2, 2017. http://www.cheminform.com/reaction-library/.
"Recommending Novel Reactants to Synthesize Chemical Products", IBM disclosure YOR8-2015-2201 filed Oct. 4, 2016 and assigned U.S. Appl. No. 15/284,612, International Business Machines Corporation, 33 pages.
"Efficient Retrosynthesis Analysis", IBM disclosure YOR8-2016-0594, filed Oct. 6, 2016 and assigned U.S. Appl. No. 15/286,972, International Business Machines Corporation, 35 pages.
Linke et al., "Systematic Methods for Working Fluid Selection and the Design, Integration and Control of Organic Rankine Cycles—A Review" Energies, 2015, pp. 4755-4801, vol. 8, 47 pages.
Ying et al., "Graph Generation with Prescribed Feature Constraints", 2009, pp. 966-977, SIAM, 12 pages.
Vijayabaskar et al., "GraProStr—Graphs of Protein Structures: A Tool for Constructing the Graphs and Generating Graph Parameters for Protein Structures", The Open Bioinformatics Journal, 2011, vol. 5, pp. 53-58, 6 pages.
Chakrabarti et al., "Graph Mining: Laws, Generators, and Algorithms", ACM Computing Surveys, Mar. 2006, vol. 38, Article 2, 69 pages.
Roe, "Structure Generation and Search Strategies" Chapter 10: Computer-Aided Molecular Design De Novo Design, Section 2.3, Handbook of Chemoinformatics Algorithms, pp. 299, 21 pages.
Loving et al., Computational Approaches for Fragment-Based and De Novo Design, Current Topics in Medicinal Chemistry, 2010, pp. 14-32, vol. 10, Bentham Science Publishers Ltd., 19 pages.
Hoksza et al., Molpher: A Software Framework for Systematic Chemical Space Exploration, Journal of Cheminformatics, 2014, vol. 6, No. 7, 13 pages.
Shang et al., "De Novo Design of Multitarget Ligands with an Iterative Fragment-Growing Strategy", Journal of Chemical Information and Modeling, 2014, pp. 1235-1241, vol. 54, ACS Publications, 7 pages.
Mell et al., "The NIST Definition of Cloud Computing," NIST Special Publication 800-145, Sep. 2011, National Institute of Standards and Technology, U.S. Department of Commerce, 7 pages.
List of IBM Patents and Applications treated as related.
Faulon, et al., "Handbook of Chemoinformatics Algorithms," © 2010 by Taylor and Francis Group, LLC, International Standard Book No. 978-1-4200-8292-0 (Hardback), 435 pages.

* cited by examiner

ITERATIVE WIDENING SEARCH FOR DESIGNING CHEMICAL COMPOUNDS

BACKGROUND

The subject disclosure relates to designing chemical compounds, and more specifically, facilitating an iterative widening search for designing chemical compounds.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, systems, computer-implemented methods, apparatus and/or computer program products that facilitate performing an iterative widening search for designing chemical compounds are described.

According to an embodiment, a computer-implemented method can comprise receiving, by a system operatively coupled to a processor, an indication of a constrained structure portion of a first chemical compound and a first unconstrained structure portion of the first chemical compound. The method can also comprise determining, by the system, a second unconstrained structure portion for the first chemical compound based on a determination that the second unconstrained structure portion satisfies a defined condition related to a difference between the first unconstrained structure portion and the second unconstrained structure portion.

According to an embodiment, a system can comprise a memory that stores computer executable components and a processor that executes computer executable components stored in the memory. The computer executable components can comprise a communication component that receives an indication of a constrained structure portion of a chemical compound and a first unconstrained structure portion of the chemical compound. The computer executable components can also comprise an analysis component that determines a second unconstrained structure portion for the chemical compound based on a determination that the second unconstrained structure portion satisfies a defined condition related to a difference between the first unconstrained structure portion and the second unconstrained structure portion.

According to another embodiment, a computer program product for facilitating an iterative widening search for designing chemical compounds can comprise a computer readable storage medium having program instructions embodied therewith. The program instructions are executable by a processing component. The program instructions can cause the processing component to evaluate a data store, which comprises one or more molecule patterns, for a molecule pattern that can be substituted for an unconstrained structure portion of a first chemical compound. The first chemical compound comprises the unconstrained structure portion and a constrained structure portion. The program instructions also can cause the processing component to generate a second chemical compound that comprises the constrained structure portion and the molecule pattern substituted for the unconstrained structure portion.

According to an implementation, the program instructions can further cause the processing component to determine a difference in one or more angles of one or more respective bonds between one or more atoms in the unconstrained structure portion and one or more other atoms in a second unconstrained structure portion. In another implementation, the program instructions can further cause the processing component to perform an iteratively widening search based on a second unconstrained structure portion, wherein the iteratively widening search is controlled by a defined condition. In yet another implementation, the program instructions can further cause the processing component to receive input data, wherein the input data is selected from a group consisting of an original compound identification, an indication of the constrained structure portion of the first chemical compound, and a defined condition.

DETAILED DESCRIPTION

Figure 1:
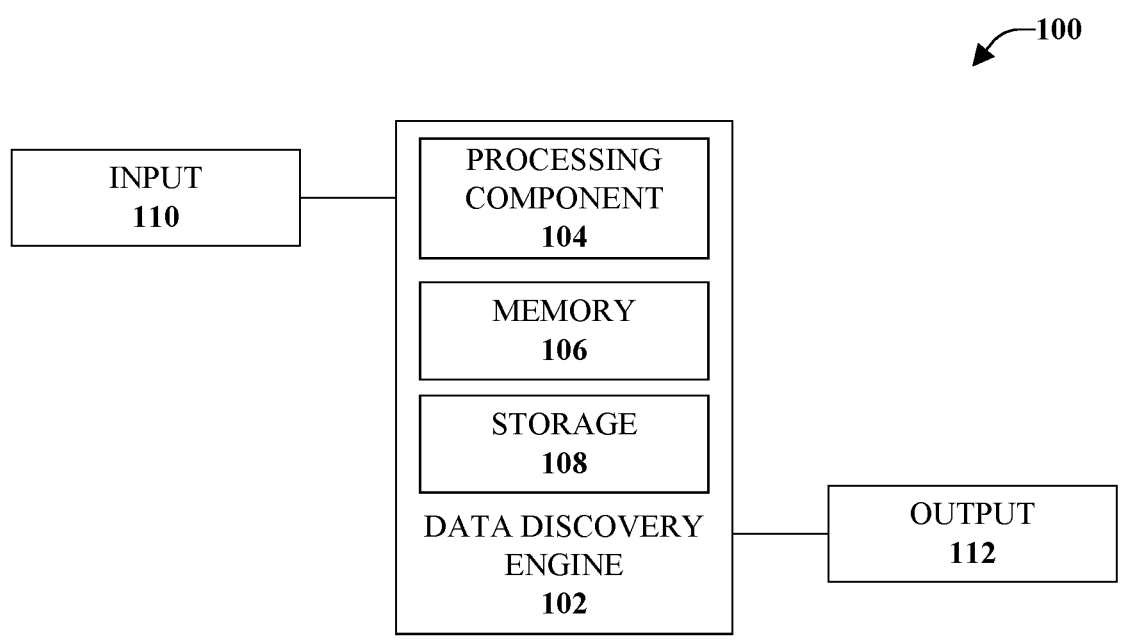
FIG. 1 illustrates a block diagram of an example, non-limiting system that facilitates an iterative widening search for designing chemical compounds in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

The various aspects provided herein relate to an iterative widening search for designing chemical compounds. The iterative widening search can provide molecules that can be substituted for one or more original molecules within the chemical compound. The substitute or alternative molecule(s) can be selected such that the substitute molecule(s) can preserve one or more desired properties of the molecule and/or the original, target chemical compound. For example, the one or more molecules selected can preserve an active part of a drug molecule (e.g., the original, target molecule) while simplifying a support part of the drug molecule. Additionally or alternatively, the one or more molecules selected can increase a yield as compared to the original, target chemical compound. According to some implementations, the various aspects can be provided as a portion of a cloud computing service, which can be utilized at various locations and by entities working independently.

In accordance with an implementation, the iterative widening search can comprise determining at least one molecule that preserves a set of constraints featured in a given sample chemical compound. To determine the at least one molecule, various inputs can be received. The inputs received can include, but are not limited to, an indication of a sample chemical compound and an indication of a constrained part of the sample chemical compound. A database that includes information related to stable molecules and unstable molecules can be utilized as a source of information. Further, a tolerance function, which can account for one or more acceptable differences between the non-constrained part of the sample chemical compound and the generated molecule can be referenced.

The iterative widening search can include performing one or several iterations where one or more iterations can return a molecule that can preserve constraints of the sample molecule. Further, a returned molecule can be selected based on a determination that the unconstrained part of the returned molecule is within a defined value of a tolerance function. According to an implementation, the defined value can be a predefined maximum value. If one or more iterations do not return an acceptable molecule (e.g., no solution is found), the defined value of the tolerance function can be adjusted. For example, the defined value (e.g., the defined maximum value) of the tolerance function can be increased.

The molecule returned in a successful iteration can become the input molecule for a next iteration. According to some implementations, interacting with an entity about a returned molecule that was returned as input of the next iteration can include modifying the returned molecule based on input received from the entity. Alternatively or additionally, the interaction can include receiving an indication that a returned molecule has been rejected. In some implementations, the interaction can include receiving a request that another molecule be returned.

According to some implementations, the one or more inputs can include a reaction chain to synthesize the sample molecule. Additionally or alternatively, the one or more inputs can include one or more constraints regarding reactions in use and substructures (e.g., toxic). In accordance with some implementations, the iterative widening search can include determining at least one reaction pathway for the molecule generated.

FIG. 1 illustrates a block diagram of an example, non-limiting system 100 that facilitates an iterative widening search for designing chemical compounds in accordance with one or more embodiments described herein. Aspects of systems (e.g., non-limiting system 100 and the like), apparatuses, or processes explained in this disclosure can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described.

In various embodiments, non-limiting system 100 can be any type of component, machine, device, facility, apparatus, and/or instrument that comprises a processor and/or can be capable of effective and/or operative communication with a wired and/or wireless network. Components, machines, apparatuses, devices, facilities, and/or instrumentalities that can comprise non-limiting system 100 can include tablet computing devices, handheld devices, server class computing machines and/or databases, laptop computers, notebook computers, desktop computers, cell phones, smart phones, consumer appliances and/or instrumentation, industrial and/or commercial devices, hand-held devices, digital assistants, multimedia Internet enabled phones, multimedia players, and the like.

As illustrated, non-limiting system 100 can comprise a data discovery engine 102, a processing component 104, a memory 106, and/or a storage 108. In some embodiments, one or more of the data discovery engine 102, the processing component 104, the memory 106, and/or the storage 108 can be communicatively and/or operatively coupled to one another to perform one or more functions of the non-limiting system 100.

The data discovery engine 102 can uncover candidate compounds that can function as expected based on one or more defined criteria. The one or more defined criteria can include, but are not limited to, properties of an identified, target molecule and/or chemical compound. The properties can include an active part of the target molecule and/or an inactive part of the target molecule. In some implementations, the one or more defined criteria can include improving a structure of a supporting part of the target molecule and/or increasing a yield of the target molecule. The yield, also referred to as reaction yield, is an amount (e.g., chemical amount) of product obtained in a chemical reaction. The product is the species formed from a chemical reaction, wherein during the chemical reaction, reactants are transformed into products after passing through a high energy transition state. By uncovering the candidate compounds, the data discovery engine 102 can facilitate implementation of one or more procedures related to new compound discovery.

In order to determine the candidate compounds, the data discovery engine 102 can receive one or more inputs 110 that comprise input data. In various embodiments, the data discovery engine 102 can receive one or more inputs related to defined chemical properties. In an example, one or more inputs can be a sample molecule including an identification of a constrained structure portion of the sample molecule. Further, one or more unconstrained structure portions of the sample molecule can be received as the one or more inputs.

In another example, the one or more inputs can include known chemical compounds including information related to stable molecules and unstable molecules. Further to this example, the information related to the known chemical compounds can be retrieved from a data store located internal to the non-limiting system 100 and/or external to the non-limiting system 100. For example, the data store can be located at, and retrievable from, a third-party trusted device.

The third party trusted device can be included in a cloud computing environment, for example. According to a further example, the one or more inputs can include a defined condition, which can be a tolerance function, which can account for acceptable differences between a non-constrained structure portion of the sample molecule and a generated molecule. In an implementation, the difference can comprise a difference in one or more angles of one or more respective bonds between one or more atoms in the first unconstrained structure portion and one or more other atoms in the second unconstrained structure portion.

According to an implementation, the input data can be selected from a group consisting of an original compound identification, an indication of the constrained structure portion of a first chemical compound, and a defined condition. In an additional or alternative implementation, the input data can be selected from a group consisting of a reaction chain and a constraint. Further to this implementation, the reaction chain can synthesize the first unconstrained portion and the constraint can be related to a reaction in use and an associated substructure.

In accordance with an embodiment, the data discovery engine 102 upon or after receiving the one or more inputs 110 can evaluate the inputs and can generate one or more recommendations related to a second unconstrained structure portion. The one or more recommendations can be provided by the data discovery engine 102 as an output 112. For example, the data discovery engine 102 can select the second unconstrained structure portion from a multitude of unconstrained structure portions. The second unconstrained structure portion can be selected by the data discovery engine 102 based on a determination that the second unconstrained structure portion satisfies a defined condition related to a difference between the first unconstrained structure portion and the second unconstrained structure portion.

For example, the non-limiting system 100 can discover new or different components that hold one or more defined chemical properties and can recommend the discovered components. The non-limiting system 100 can search for a new or different molecule that can preserve a partially constrained structure. Further, the non-limiting system 100 can employ an iterative widening search that can be controlled by the tolerance function. The iterative widening search can be performed based on the second unconstrained structure portion and can be controlled by the defined condition.

In some implementations, the non-limiting system 100 can generate a second chemical compound that comprises the constrained structure portion and the second unconstrained structure portion. Further to this implementation, the non-limiting system 100 can determine a third unconstrained structure portion for the first chemical compound. The third unconstrained structure portion can be determined based on another determination that the third unconstrained structure portion satisfies the defined condition related to the difference between the second unconstrained structure portion and the third unconstrained structure portion.

Discovery of new or different chemical compounds can be useful in various industries including, for example, pharmaceutical, chemical, food, and/or material industries. In an example of a chemical industry, candidate compounds can be designed and the efficacy and side effects can be experimentally validated (e.g., development of new medicine for heart disease). The design and evaluation of new compounds can involve many trials and errors, most of which end up with failures (e.g., success rate of generating a new drug is estimated to be less than one percent). For example, when forming new chemical compounds, researchers solve what is needed for the reaction manually by designing a target chemical compound and attempt to determine what the set of required reactants are to form a pathway for generating the target. This is a time-consuming task that can contain human error such as failing to determine solutions or finding only suboptimal solutions. The various aspects provided herein recommend candidate compounds that function as expected, thus facilitating compound discovery and increase the success rate of generating a new drug.

The computer processing systems, computer-implemented methods, apparatus and/or computer program products employ hardware and/or software to solve problems that are highly technical in nature (e.g., related to determination of alternative unconstrained structure portions related to designing chemical compounds, performing an iteratively widening search related to the alternative unconstrained structure portions, determining differences between one or more angles of one or more respective bonds between one or more atoms in first unconstrained structure portions), that are not abstract and that cannot be performed as a set of mental acts by a human. For example, a human, or even thousands of humans, cannot efficiently, accurately and effectively manually analyze the voluminous amounts of structural portions of chemical compounds that can be utilized as suitable alternatives without performing a multitude of experiments, which is time consuming and might never be successfully performed. Thus, the one or more embodiments of the subject computer processing systems, methods, apparatuses and/or computer program products can enable the automated determination of suitable alternatives of unconstrained structure portions of a target chemical compound. Even with a significant advance of computer hardware technologies, discovering a new compound has been a difficult task due to a very large number of possible compound structures that need to be considered. The various aspects provided herein narrow the search space to consider, with the help of a tolerance function and iterative widening that enable focus on the promising portions of the search space where compounds that are similar to the original compound are located.

Figure 2:
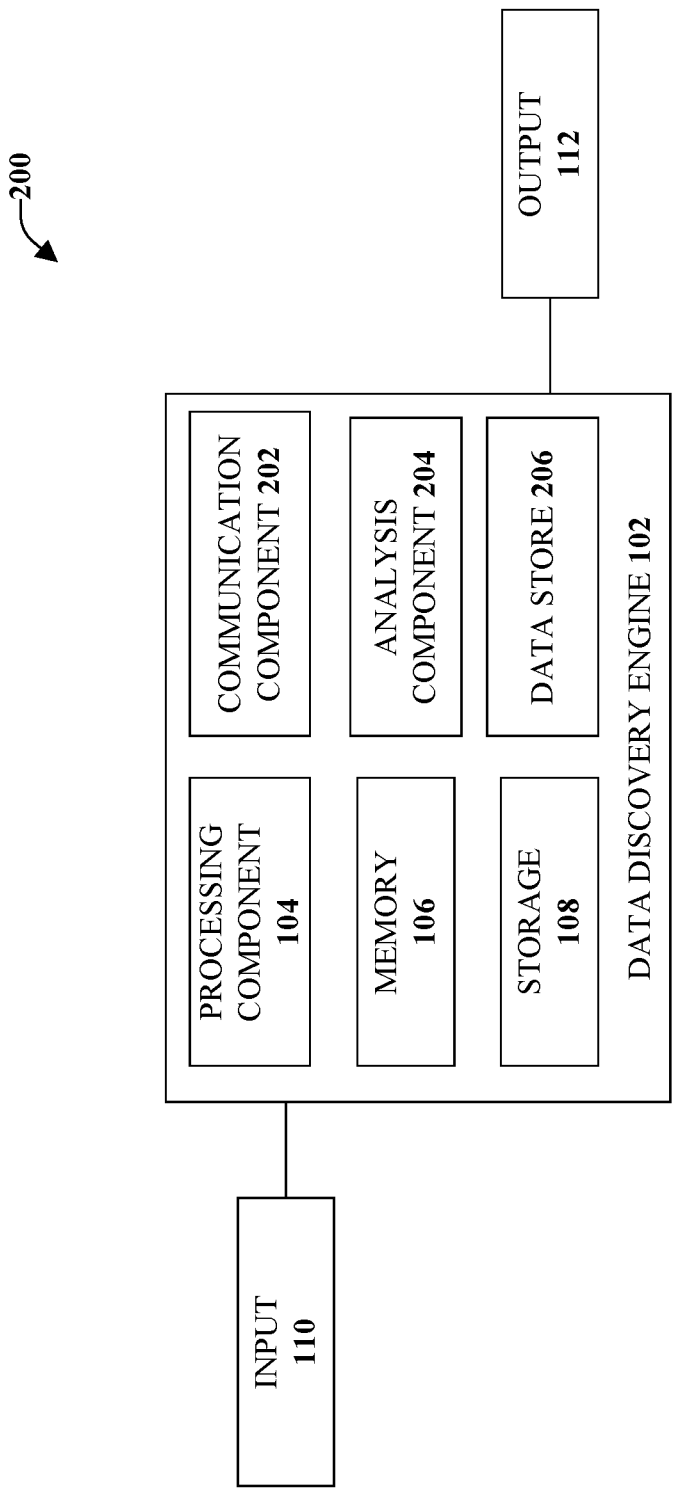
FIG. 2 illustrates a block diagram of an example, non-limiting system that facilitates chemical compound determinations in accordance with one or more embodiments described herein.

FIG. 2 illustrates a block diagram of an example, non-limiting system 200 that facilitates chemical compound determinations in accordance with one or more embodiments described herein. Repetitive description of like elements employed in other embodiments described herein is omitted for sake of brevity. The non-limiting system 200 can comprise one or more of the components and/or functionality of non-limiting system 100, and vice versa. As illustrated, the data discovery engine 102 of non-limiting system 200 can comprise a communication component 202, an analysis component 204, and a data store 206.

The communication component 202 can receive as input 110, for a first chemical compound, an indication of a constrained structure portion and a first unconstrained structure portion. The first chemical compound can be an original or target chemical compound for which a substitute is desired. Active drug molecules can comprise active parts and structure supporting parts. According to the various aspects provided herein, the structure supporting parts can be made simpler, which can make synthesis easier. Thus, is can be beneficial to design a molecule with simpler structures to facilitate synthesis. The various aspects can automatically find the simpler structures and provide a recommendation related to the simpler structures.

The indication of the constrained structure portion and the first unconstrained structure portion can be received from an entity, for example. As utilized herein an "entity" can be one or more computers, the Internet, one or more systems, one or more commercial enterprises, one or more computers, one or more computer programs, one or more machines, machinery, one or more actors, one or more users, one or ore more customers, one or more humans, and so forth, hereinafter referred to as an "entity" or "entities," depending on the context.

Based on the indication (e.g., the input 110) received at the communication component 202, the analysis component 204 can determine an alternative unconstrained structure portion for the first chemical compound. For example, the analysis component 204 can access the data store 206, which can include information related to one or more chemical properties of stable molecules and/or one or more chemical properties of an unstable molecules. The analysis component 204 can compare the chemical properties and select one more molecules that can be utilized as an alternative unconstrained structure portion. Based on the alternative unconstrained structure portion determined by the analysis component 204, a new chemical compound can be created. The new chemical compound can include the original constrained structure portion of the first chemical compound, and the alternative unconstrained structure portion.

The information related to the alternative unconstrained structure portion can be provided as the output 112 by the communication component 202. The output 112 facilitated by the communication component 202 can be in various electronic formats including visually, such as on a display screen and/or audibly, such as through speakers or headphones. According to some implementations, the output 112 can include audio information, such as information related to the alternative unconstrained structure portion. Circuitry to generate the audio output can be included on a motherboard or a sound card coupled to a set of external speakers or headphones.

According to some implementations, the input 110 can pinpoint the type of problem being solved. A sample molecule can be received together with information about what parts should be preserved (active part or constrained part) and what parts should be improved (support part or unconstrained part). Once the problem type is identified, tests can be devised. A test can include observing the correlation between the computational time and the similarity between the original molecule and the resulting molecule. A shorter computational time correlated with a stronger similarity can indicate the use of a widening search, as discussed herein. According to another test, when thresholds are configurable and entered (as opposed to automatically being determined), the correlation between the threshold, the similarity between the two molecules, and the computational time can be observed.

Figure 3:
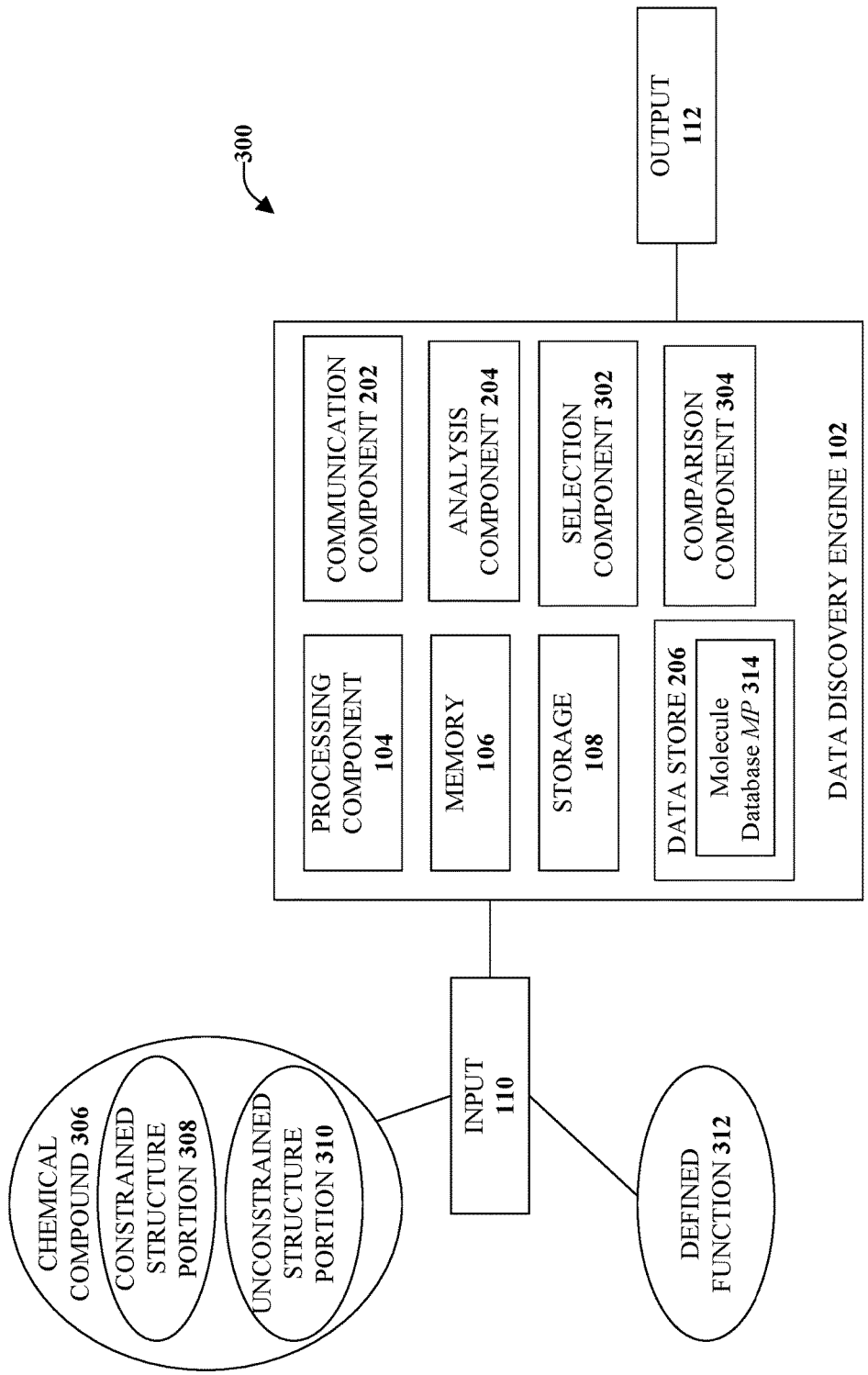
FIG. 3 illustrates a block diagram of an example, non-limiting system that facilitates discovery of new chemical compounds based on one or more defined parameters in accordance with one or more embodiments described herein.

FIG. 3 illustrates a block diagram of an example, non-limiting system 300 that facilitates discovery of new chemical compounds based on one or more defined parameters in accordance with one or more embodiments described herein. Repetitive description of like elements employed in other embodiments described herein is omitted for sake of brevity. The non-limiting system 300 can comprise one or more of the components and/or functionality of non-limiting system 100 and or non-limiting system 200, and vice versa. As illustrated, the data discovery engine 102 of the non-limiting system 300 can comprise a selection component 302 and a comparison component 304.

The communication component 202 can receive, as an input of the one or more inputs 110, information related to a candidate chemical compound, referred to as an original chemical compound 306, which can include at least one constrained portion 308 and at least one unconstrained portion 310. According to some implementations, identification of at least one constrained portion 308 and at least one unconstrained portion 310 can be received in lieu of the indication of the original chemical compound 306.

According to some implementations, a tolerance function or a defined function 312 can be received as an input. The defined function 312 can be denoted as f. The defined function 312 can be selected based on the indication of the original chemical compound 306, the at least one constrained portion 308, and/or the at least one unconstrained portion 310. For example, a first defined function for a first original chemical compound can be different than a second defined function for a second original chemical compound. However, according to some implementations, a defined function can be the same for a first original chemical compound and a second original chemical compound.

Upon or after receipt of the at least one unconstrained portion 310, the at least one constrained portion 308, and the defined function 312 by the communication component 202, the selection component 302 can select a set of molecule patterns MP from a molecule database MD 314. The molecule database MD 314 can be included in the data store 206 as illustrated. However, according to some implementations, the molecule database MD 314 can be included in another non-limiting system 300 component, or can be included in a component external to the non-limiting system 300.

In an example, the selection component 302 can select molecule patterns from the molecule database MD 314. The determination of which molecule patterns to select can be based on those molecule patterns that can obtain a higher value of preference from function g than the at least one unconstrained portion 310 of the original chemical compound 306 that is to be replaced and improved. For example, the selection component 302 can split the original chemical compound 306 into the at least one constrained portion 308 and the at least one unconstrained portion 310. The at least one constrained portion 308 can be denoted as C and the at least one unconstrained portion 310 can be denoted as S.

In an example, the selection component 302 can determine the value of preference of a molecule pattern by counting the number of atoms in the pattern. In another example, the selection component 302 can determine the value of preference based on the occurrence of van-der-Waals interactions (e.g., Hydrogen-bonds opposite to lone electron pairs).

The comparison component 304 can implement the defined function 312. For example, the defined function 312 (also referred to as tolerance function) can be denoted as $f(X,Y)$. The comparison component 304 can use the defined function 312 to evaluate or check a difference in angles of bonds between atoms in molecules X and Y. For example, molecule X can be an original unconstrained structure portion and molecule Y can be a possible alternative unconstrained structure portion. Based on this evaluation, the comparison component 304 can return a single value as a result.

The comparison component 304 can quickly estimate a molecule's geometry using various techniques. For example, the comparison component 304 can apply Valence Shell Electron Pair Repulsion (VSEPR) theory to estimate the molecule's geometry. VSEPR theory is a model used in chemistry to determine the geometry of individual molecules from a number of electrons pairs surrounding their central atoms. The premise of VSEPR theory is that valence electron pairs that surround an atom tend to repel and, therefore, can adopt an arrangement that minimizes the repulsion and, thus, determine the molecule's geometry.

In another example, the comparison component 304 can apply molecular dynamics based methods to estimate a molecule's geometry. Molecular dynamics use a computer simulation method for studying physical movements of atoms and molecules, which are permitted to interact for a defined period of time. During the defined period of time, the interaction of the atoms and molecules are observed and trajectories can be determined. In another example, during the defined period of time, forces between the particles and their potential energies can be calculated.

According to an implementation, the system 300 can use as input a sample molecule with its structure logically separated into a constrained (e.g., active) part and an unconstrained (e.g., support) part. Based on the sample molecule, the goal can be to create another molecule with the same active part but with a "better" support part, where better can mean simpler or easier to synthesize. Using a sample molecule, the various aspects can speed up the search for the new molecule.

In accordance with an implementation, to construct a new unconstrained structure E a search in search space of the set of molecular patterns MPs can be performed to find replacements for a segment m that increases the value of preference of the final molecule. The original unconstrained structure S can be split into several segments s and one or several parts of the original unconstrained structure S can be replaced by a new pattern found in the set of molecular patterns MPs. Further, the original unconstrained structure S can be split, for example, based on the original synthesis pathway from literature or can be obtained by a retrosynthethic analysis solver, based on a library of known reaction rules compiled from literature, human input through a user interface, and so on. Molecular patterns MPs and segments s can be modified according to a reaction pattern database to enable connections (bonding) to existing segments s. As an additional procedure, checking a stability of molecules could be added to discard unstable candidate molecules in one or more steps in accordance with various embodiments.

Figure 4:
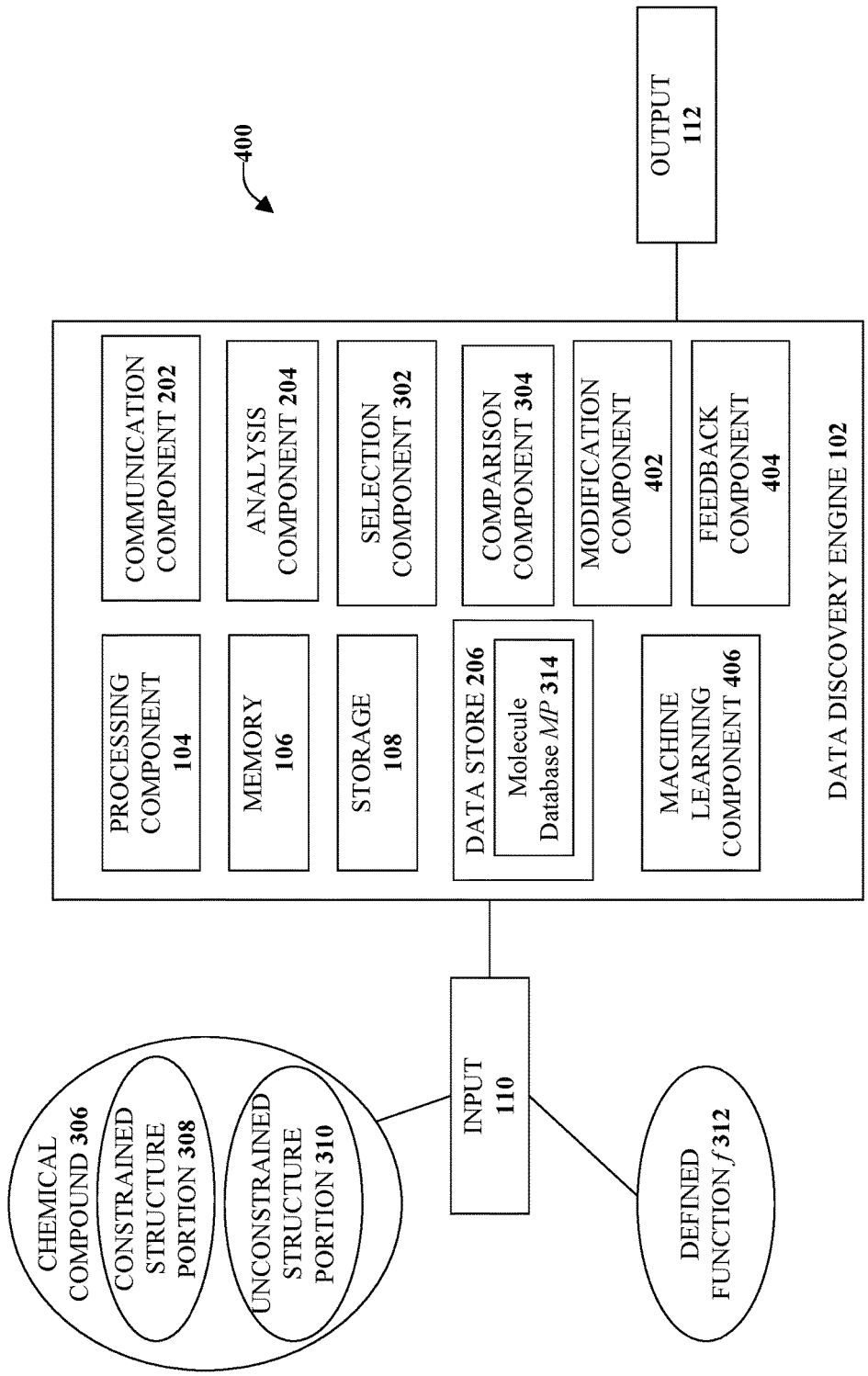
FIG. 4 illustrates a block diagram of an example, non-limiting system that utilizes a feedback loop to return one or more results related to alternative chemical compounds in accordance with one or more embodiments described herein.

FIG. 4 illustrates a block diagram of an example, non-limiting system 400 that utilizes a feedback loop to return one or more results related to alternative chemical compounds in accordance with one or more embodiments described herein. Repetitive description of like elements employed in other embodiments described herein is omitted for sake of brevity. The non-limiting system 400 can comprise one or more of the components and/or functionality of non-limiting system 100, non-limiting system 200, and/or non-limiting system 300 and vice versa. As illustrated, the data discovery engine 102 of non-limiting system 400 can comprise a modification component 402, a feedback component 404, and a machine learning component 406.

The modification component 402 can adjust one or more values related to the defined function 312. For example, the defined function 312 can indicate that a difference of angles of bonds between atoms of a first unconstrained portion should be within a first value of the angles of bonds between atoms of a second unconstrained portion. However, in some cases there might be no results discovered by the analysis component 204 and/or the selection component 302 that conform to that first value. In this situation, the modification component 402 can determine a second value for the defined function 312 that should be used to evaluate the difference. The second value can be a value selected to return at least one result. In a specific example, the first value can be thirty degrees and the second value can be sixty degrees. If still no results are discovered, a third value can be selected for the defined function 312. Continuing the above example where the second value is sixty degrees, the third value selected can be ninety degrees.

When an acceptable alternative for the unconstrained structure portion is determined, a new chemical compound can be generated that comprises the constrained structure portion and the alternative unconstrained structure portion (referred to as a result). The feedback component 404 can return the result and input the result as an input that is a substitute for the original compound, or a modified original compound. In such a manner, rather than determining unconstrained portions for the original compound, the modified original compound is used to determine another unconstrained portion that can be utilized as an alternative. Thus, on a second search, instead of starting the search with the original compound, the search is started with the modified original compound.

Further, in an embodiment, the machine learning component 406 can perform a set of machine learning computations associated with the one or more inputs 110 and/or the one or more outputs 112. For example, the machine learning component 406 can determine one or more alternative unconstrained structure portions for the chemical compound, a defined tolerance function, and a modified defined tolerance function based on a determination that no acceptable unconstrained structure portions satisfied the defined tolerance function. According to another example, the machine learning component 406 can evaluate parameters of the one or original chemical compound and/or a modified chemical compound and facilitate output of a recommended unconstrained structure portion(s) that could be utilized for an alternative to an original unconstrained structure portion. Further, the machine learning component 406 can evaluate the performance of the alternative unconstrained structure portion and recommend a different unconstrained structure portion if the performance of the alternative unconstrained structure portion does not meet an acceptable performance level based on a modeled or simulated performance not performing as expected.

The machine learning component 406 can utilize machine learning systems that have been explicitly or implicitly trained to learn, determine or infer a target molecule given a constrained substructure that could be in the active area, automatically design and recommend the target molecule, and so on, that achieve desired properties with consideration of a computation time and a similarity between an original molecule and the resulting molecule, and so on. It is to be appreciated that machine learning systems can be implemented in one or more of the components to generate explicitly and/or implicitly trained models that can provide the recommendation outputs that are determined to preserve an active part of a sample molecule while improving a supporting part of the molecule. The machine learning systems can learn systems, networks, etc., identify constrained portions of a chemical compound, identify unconstrained portions of the chemical compound, identify suitable alternatives for the unconstrained portions of the chemical compound that can be utilized to increase efficiency of new compound discovery.

According to some implementations, the communication component 202 can facilitate he output 112 at respective devices of one or more entities that provided the one or more inputs 1120. The respective devices can comprise one or more computing devices as well as other interface components, which can provide a graphical user interface (GUI), a command line interface, a speech interface, Natural Language text interface, and the like. For example, a Graphical User Interface (GUI) can be rendered that provides a user with a region or means to load, import, select, read, and so forth, various requests and can include a region to present the results of the various requests. These regions can include known text and/or graphic regions that include dialogue boxes, static controls, drop-down-menus, list boxes, pop-up menus, as edit controls, combo boxes, radio buttons, check boxes, push buttons, graphic boxes, and so on. In addition, utilities to facilitate the information conveyance, such as vertical and/or horizontal scroll bars for navigation and toolbar buttons to determine whether a region will be viewable, can be employed. Thus, it might be inferred that the user did want the action performed.

The user can also interact with the regions to select and provide information through various devices such as a mouse, a roller ball, a keypad, a keyboard, a pen, gestures captured with a camera, a touch screen, and/or voice activation, for example. According to an aspect, a mechanism, such as a push button or the enter key on the keyboard, can be employed subsequent to entering the information in order to initiate information conveyance. However, it is to be appreciated that the disclosed aspects are not so limited. For example, merely highlighting a check box can initiate information conveyance. In another example, a command line interface can be employed. For example, the command line interface can prompt the user for information by providing a text message, producing an audio tone, or the like. The user can then provide suitable information, such as alphanumeric input corresponding to an option provided in the interface prompt or an answer to a question posed in the prompt. It is to be appreciated that the command line interface can be employed in connection with a GUI and/or Application Program Interface (API). In addition, the command line interface can be employed in connection with hardware (e.g., video cards) and/or displays (e.g., black and white, and Video Graphics Array (EGA)) with limited graphic support, and/or low bandwidth communication channels.

Figure 5:
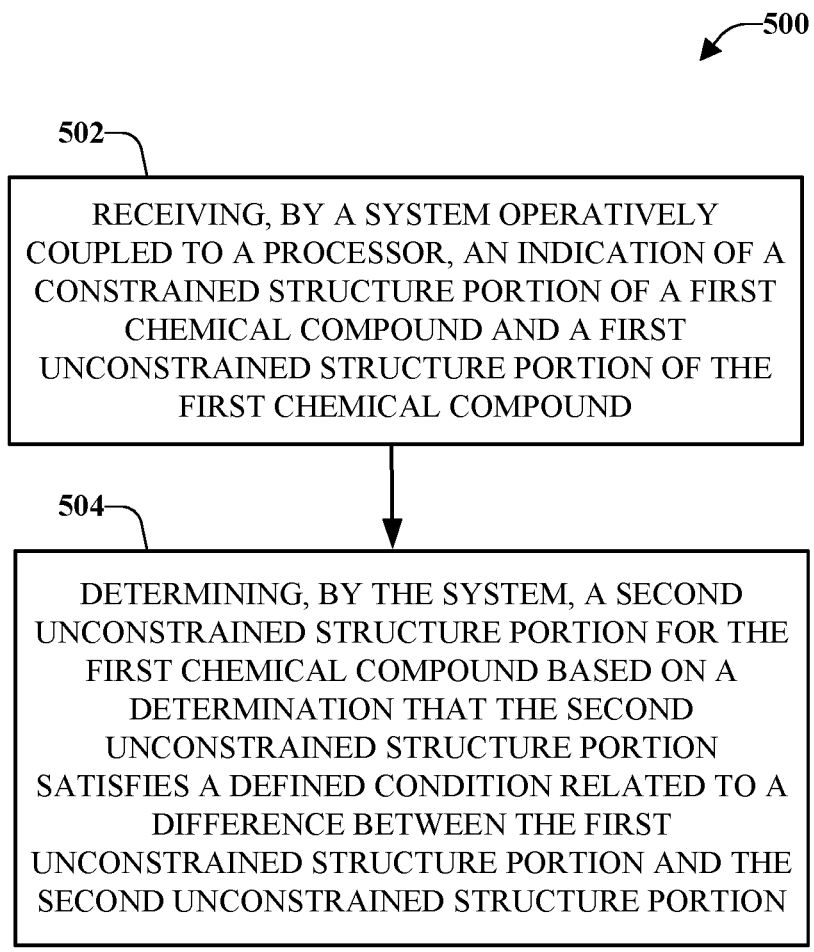
FIG. 5 illustrates a flow diagram of an example, non-limiting computer-implemented method that facilitates designing chemical compounds in accordance with one or more embodiments described herein.

FIG. 5 illustrates a flow diagram of an example, non-limiting computer-implemented method 500 that facilitates designing chemical compounds in accordance with one or more embodiments described herein. The various aspects discussed herein can improve chemical compound discovery by constructing a new unconstrained structure of the molecule while preserving a constrained structure of the molecule. In an example, the constrained structure can be specified by an entity, such as a chemist. Further, the various aspects can employ an iterative widening search, which can gradually widen the search space. The iterative widening search can be controlled by a tolerance function. In addition, a returned molecule can be provided as input to the next iteration to search for a further alternative molecule. Accordingly, the various aspects can systematically focus on the promising portions of the search space.

The non-limiting computer-implemented method 500 starts, at 502, when a system operatively coupled to a processor, can receive one or more inputs related to a search for designing chemical compounds (e.g., via the communication component 202). According to an implementation, the one or more inputs can comprise an indication of a constrained structure portion of a first chemical compound and an indication of a first unconstrained structure portion of the first chemical compound.

At 504, the system can determine a second unconstrained structure portion for the first chemical compound (e.g., via the analysis component 204). The determination of the second unconstrained portion can be based on a determination that the second unconstrained structure portion satisfies a defined condition related to a difference between the first unconstrained structure portion and the second unconstrained structure portion. In an example, the difference can comprise a difference in one or more angles of one or more respective bonds between one or more atoms in the first unconstrained structure portion and one or more other atoms in the second unconstrained structure portion.

Figure 6:
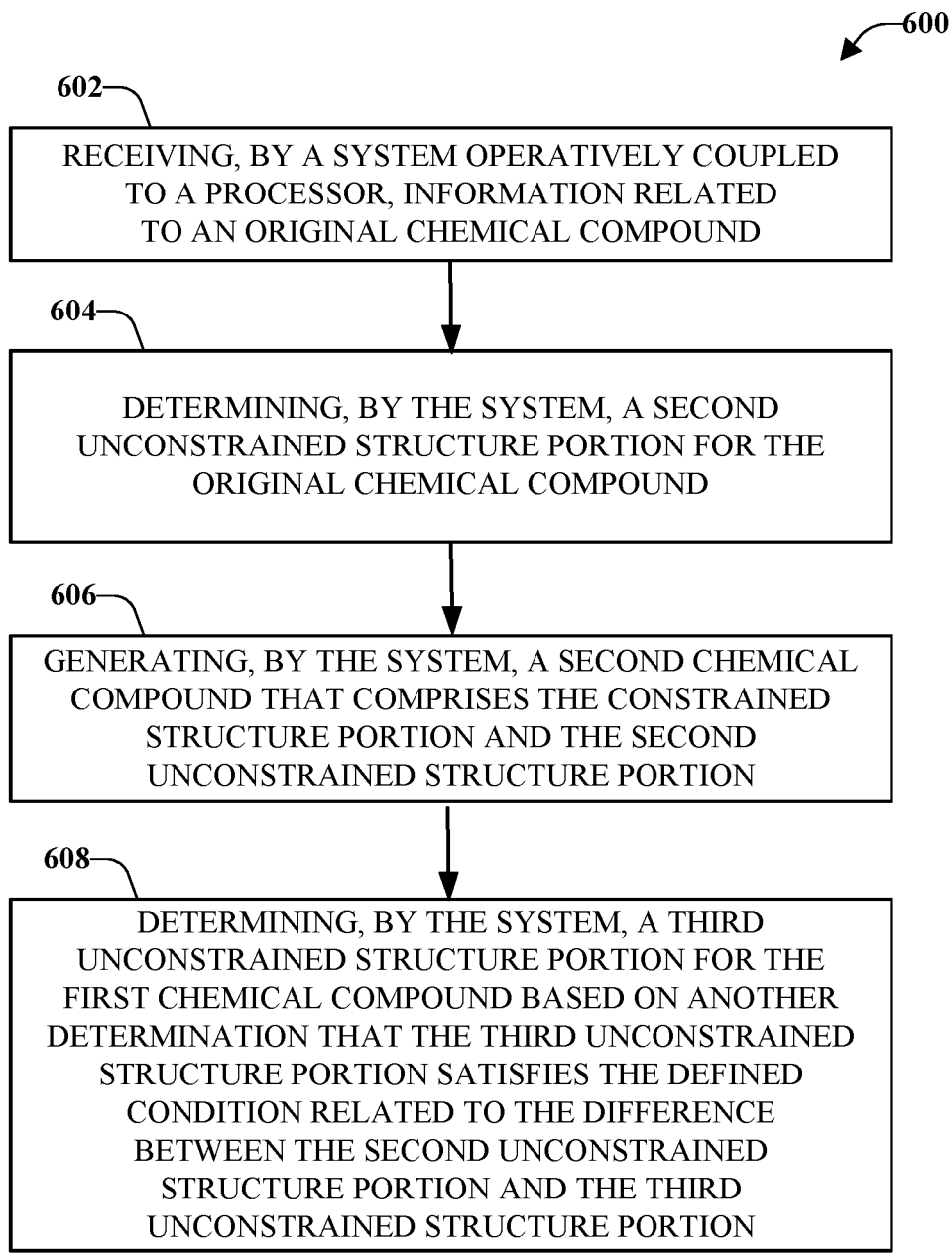
FIG. 6 illustrates a flow diagram of an example, non-limiting computer-implemented method that facilitates iterative widening searches in accordance with one or more embodiments described herein.

FIG. 6 illustrates a flow diagram of an example, non-limiting computer-implemented method 600 that facilitates iterative widening searches in accordance with one or more embodiments described herein. At 602, a system operatively coupled to a processor, can receive information related to an original chemical compound (e.g., via the communication component 202). The information can include an indication of constrained structure portions and/or unconstrained structure portions of the original chemical compound. The constrained structure portions can comprise active parts of the original chemical compound. The unconstrained structure portions can be supporting portions of the chemical compound that can be made simpler, resulting in easier synthesis. The unconstrained structure portions can be identified for replacement while preserving the constrained structure portions.

A second unconstrained structure portion, to replace a first unconstrained structure portion in the original compound, can be determined, at 604 (e.g., via the comparison component 304). For example, the second unconstrained structure portion can be determined to satisfy a defined tolerance function. At 606, a second chemical compound that comprises the constrained structure portion and the second unconstrained structure portion can generated (e.g., via the selection component 302).

Further, at 608, a third unconstrained structure portion for the first chemical compound can be determined (e.g., via the analysis component 204). The determination can be based on the third unconstrained structure portion satisfying the defined condition related to the difference between the second unconstrained structure portion and the third unconstrained structure portion.

Figure 7:
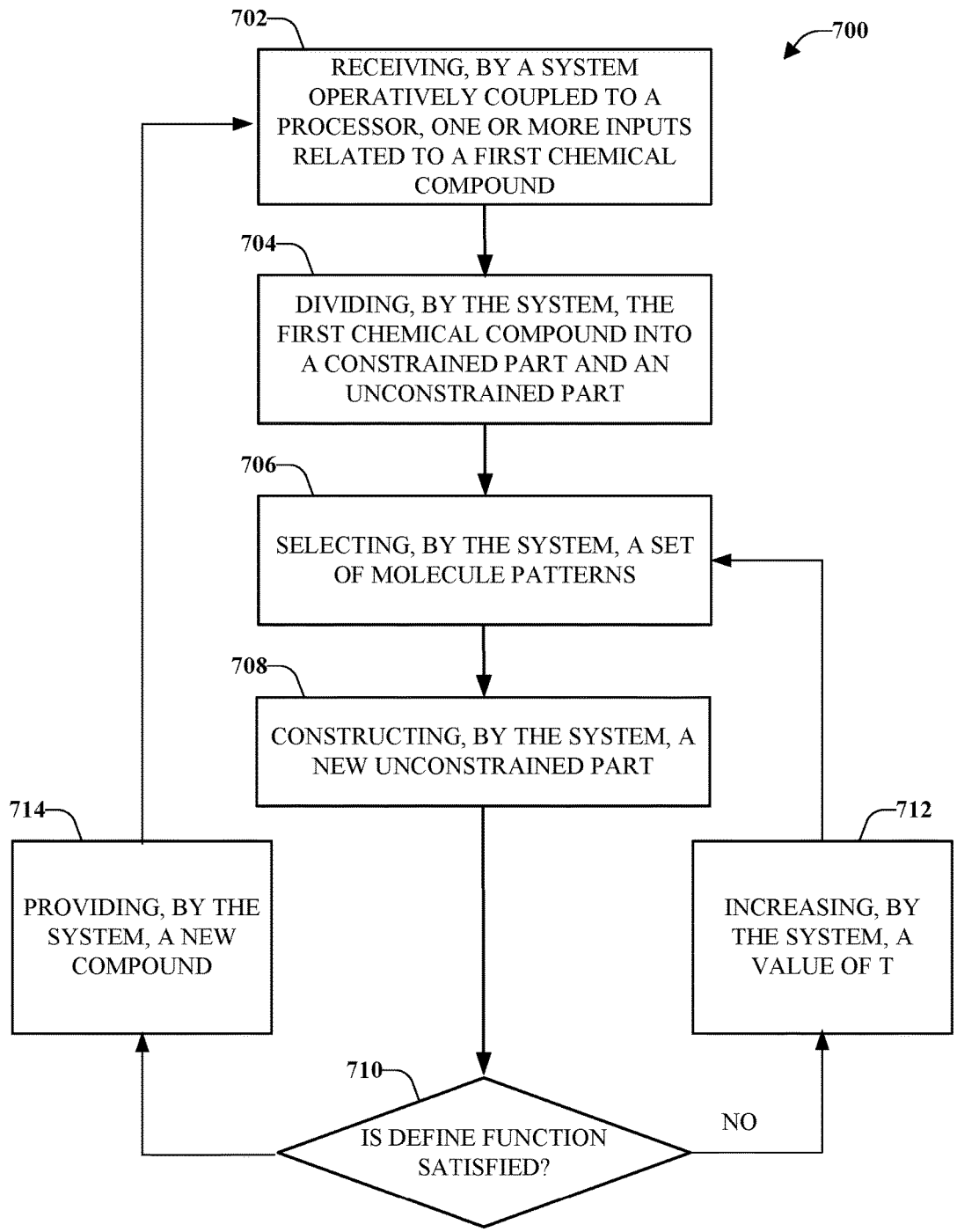
FIG. 7 illustrates a flow diagram of an example, non-limiting computer-implemented method that facilitates an iterative widening search for designing chemical compounds in accordance with one or more embodiments described herein.

FIG. 7 illustrates a flow diagram of an example, non-limiting computer-implemented method 700 that facilitates an iterative widening search for designing chemical compounds in accordance with one or more embodiments described herein. At 702, a system operatively coupled to a processor, receives one or more inputs related to a first chemical compound (e.g., via the communication component). The one or more inputs can include an indication of an original compound O (e.g., the first chemical compound) and a constrained part C of the original compound O. The one or more inputs can also include a defined function, such as a tolerance function $f$. According to some implementations, the input can be one or more molecule databases MDs. According to other implementations, the system can have access to the one or more molecule databases MDs that are maintained in a cloud computing environment, for example.

Upon or after receipt of the indication of the original compound O, the method is initialized at time t. At 704, the original compound O can be divided into its constrained part C and its unconstrained part S (e.g., via the analysis component 204). According to some implementations, the indication of the unconstrained part S of the original compound O can be received as one of the inputs, at 702.

At 706, a set of molecule patterns MPs can be selected (e.g., via the selection component 302). For example, the one or more molecule databases MDs can be accessed to select the set of molecule patterns MP. According to some implementations, the one or more molecule databases MDs can be accessed to determine a match for the unconstrained part S of the original compound O.

A new unconstrained structure E can be constructed at 708 (e.g., via the analysis component 204). Constructing the new unconstrained structure E can include constructing a new unconstrained structure that satisfies the equation $f(S, E)<t$. For example, the equation can be satisfied by using molecule patterns MP selected from the molecule database MD. At determination is made, at 710, whether the selected molecule pattern MP satisfies the defined function. If the selected molecule pattern MP does not satisfy the defined function ("NO"), a value of t can be increased, at 712 (e.g., via the modification component 402). The non-limiting computer-implemented method 700 continues at 706 and another set of molecule patterns MP can be selected from the molecule database MD.

If the determination is that the selected molecule pattern MP satisfies the defined function ("YES"), at 714, a new compound P is generated (e.g., via the feedback component 404). The new compound P can input to the system at 702 and used to discover further chemical compounds.

For simplicity of explanation, the computer-implemented methodologies are depicted and described as a series of acts. It is to be understood and appreciated that the subject innovation is not limited by the acts illustrated and/or by the order of acts, for example acts can occur in various orders and/or concurrently, and with other acts not presented and described herein. Furthermore, not all illustrated acts can be required to implement the computer-implemented methodologies in accordance with the disclosed subject matter. In addition, those skilled in the art will understand and appreciate that the computer-implemented methodologies could alternatively be represented as a series of interrelated states via a state diagram or events. Additionally, it should be further appreciated that the computer-implemented methodologies disclosed hereinafter and throughout this specification are capable of being stored on an article of manufacture to facilitate transporting and transferring such computer-implemented methodologies to computers. The term article of manufacture, as used herein, is intended to encompass a computer program accessible from any computer-readable device or storage media.

Figure 8:
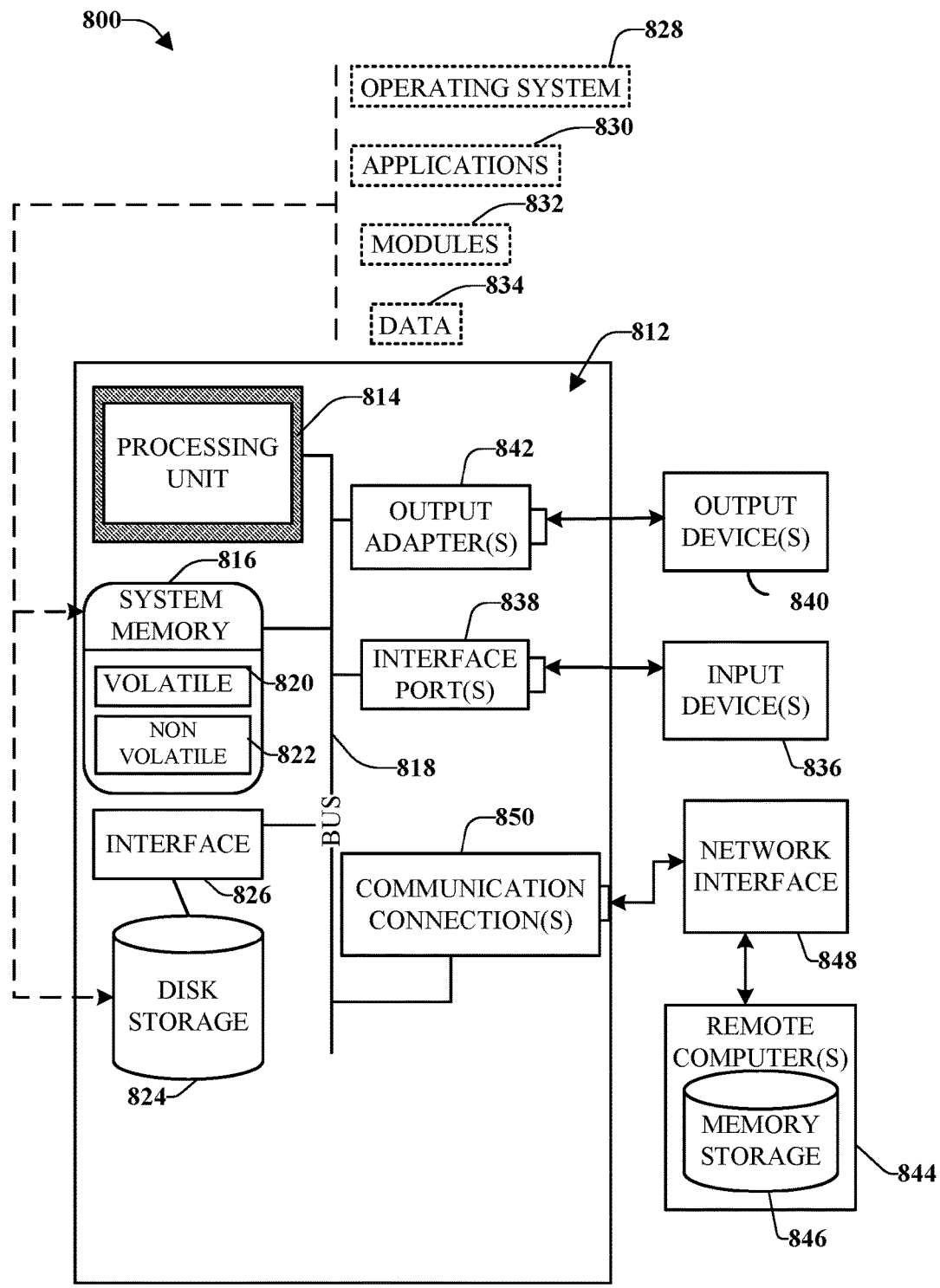
FIG. 8 illustrates a block diagram of an example, non-limiting operating environment in which one or more embodiments described herein can be facilitated.

In order to provide a context for the various aspects of the disclosed subject matter, FIG. 8 as well as the following discussion are intended to provide a general description of a suitable environment in which the various aspects of the disclosed subject matter can be implemented. FIG. 8 illustrates a block diagram of an example, non-limiting operating environment in which one or more embodiments described herein can be facilitated. Repetitive description of like elements employed in other embodiments described herein is omitted for sake of brevity. With reference to FIG. 8, a suitable operating environment 800 for implementing various aspects of this disclosure can also include a computer 812. The computer 812 can also include a processing unit 814, a system memory 816, and a system bus 818. The system bus 818 couples system components including, but not limited to, the system memory 816 to the processing unit 814. The processing unit 814 can be any of various available processors. Dual microprocessors and other multiprocessor architectures also can be employed as the processing unit 814. The system bus 818 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire (IEEE 1394), and Small Computer Systems Interface (SCSI). The system memory 816 can also include volatile memory 820 and nonvolatile memory 822. The basic input/output system (BIOS), containing the basic routines to transfer information between elements within the computer 812, such as during start-up, is stored in nonvolatile memory 822. By way of illustration, and not limitation, nonvolatile memory 822 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM). Volatile memory 820 can also include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 812 can also include removable/non-removable, volatile/non-volatile computer storage media. FIG. 8 illustrates, for example, a disk storage 824. Disk storage 824 can also include, but is not limited to, devices like a magnetic disk drive, floppy disk drive, tape drive, Jaz drive, Zip drive, LS-100 drive, flash memory card, or memory stick. The disk storage 824 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 824 to the system bus 818, a removable or non-removable interface is typically used, such as interface 826. FIG. 8 also depicts software that acts as an intermediary between users and the basic computer resources described in the suitable operating environment 800. Such software can also include, for example, an operating system 828. Operating system 828, which can be stored on disk storage 824, acts to control and allocate resources of the computer 812. System applications 830 take advantage of the management of resources by operating system 828 through program modules 832 and program data 834, e.g., stored either in system memory 816 or on disk storage 824. It is to be appreciated that this disclosure can be implemented with various operating systems or combinations of operating systems. A user enters commands or information into the computer 812 through input device(s) 836. Input devices 836 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 814 through the system bus 818 via interface port(s) 838. Interface port(s) 838 include, for example, a serial port, a parallel port, a game port, and a universal serial bus (USB). Output device(s) 840 use some of the same type of ports as input device(s) 836. Thus, for example, a USB port can be used to provide input to computer 812, and to output information from computer 812 to an output device 840. Output adapter 842 is provided to illustrate that there are some output devices 840 like monitors, speakers, and printers, among other output devices 840, which require special adapters. The output adapters 842 include, by way of illustration and not limitation, video and sound cards that provide a method of connection between the output device 840 and the system bus 818. It should be noted that other devices and/or systems of devices provide both input and output capabilities such as remote computer(s) 844.

Computer 812 can operate in a networked environment using logical connections to one or more remote computers, such as remote computer(s) 844. The remote computer(s) 844 can be a computer, a server, a router, a network PC, a workstation, a microprocessor based appliance, a peer device or other common network node and the like, and typically can also include many or all of the elements described relative to computer 812. For purposes of brevity, only a memory storage device 846 is illustrated with remote computer(s) 844. Remote computer(s) 844 is logically connected to computer 812 through a network interface 848 and then physically connected via communication connection 850. Network interface 848 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). Communication connection(s) 850 refers to the hardware/software employed to connect the network interface 848 to the system bus 818. While communication connection 850 is shown for illustrative clarity inside computer 812, it can also be external to computer 812. The hardware/software for connection to the network interface 848 can also include, for exemplary purposes only, internal and external technologies such as, modems including regular telephone grade modems, cable modems and DSL modems, ISDN adapters, and Ethernet cards.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models. The characteristics are as follows: on-demand self-service: a cloud consumer can unilaterally provision computing capabilities, such as server time and network storage, as needed automatically without requiring human interaction with the service's provider. Broad network access: capabilities are available over a network and accessed through standard mechanisms that promote use by heterogeneous thin or thick client platforms (e.g., mobile phones, laptops, and PDAs). Resource pooling: the provider's computing resources are pooled to serve multiple consumers using a multi-tenant model, with different physical and virtual resources dynamically assigned and reassigned according to demand There is a sense of location independence in that the consumer generally has no control or knowledge over the exact location of the provided resources but may be able to specify location at a high level of abstraction (e.g., country, state, or data center). Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time. Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows: Software as a Service (SaaS): the capability provided to the consumer is to use the provider's applications running on a cloud infrastructure. The applications are accessible from various client devices through a thin client interface such as a web browser (e.g., web-based e-mail) The consumer does not manage or control the underlying cloud infrastructure including network, servers, operating systems, storage, or even individual application capabilities, with the possible exception of limited user-specific application configuration settings. Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations. Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of selected networking components (e.g., host firewalls).

Deployment Models are as follows: Private cloud: the cloud infrastructure is operated solely for an organization. It may be managed by the organization or a third party and may exist on-premises or off-premises. Community cloud: the cloud infrastructure is shared by several organizations and supports a specific community that has shared concerns (e.g., mission, security requirements, policy, and compliance considerations). It may be managed by the organizations or a third party and may exist on-premises or off-premises. Public cloud: the cloud infrastructure is made available to the general public or a large industry group and is owned by an organization selling cloud services. Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 9:
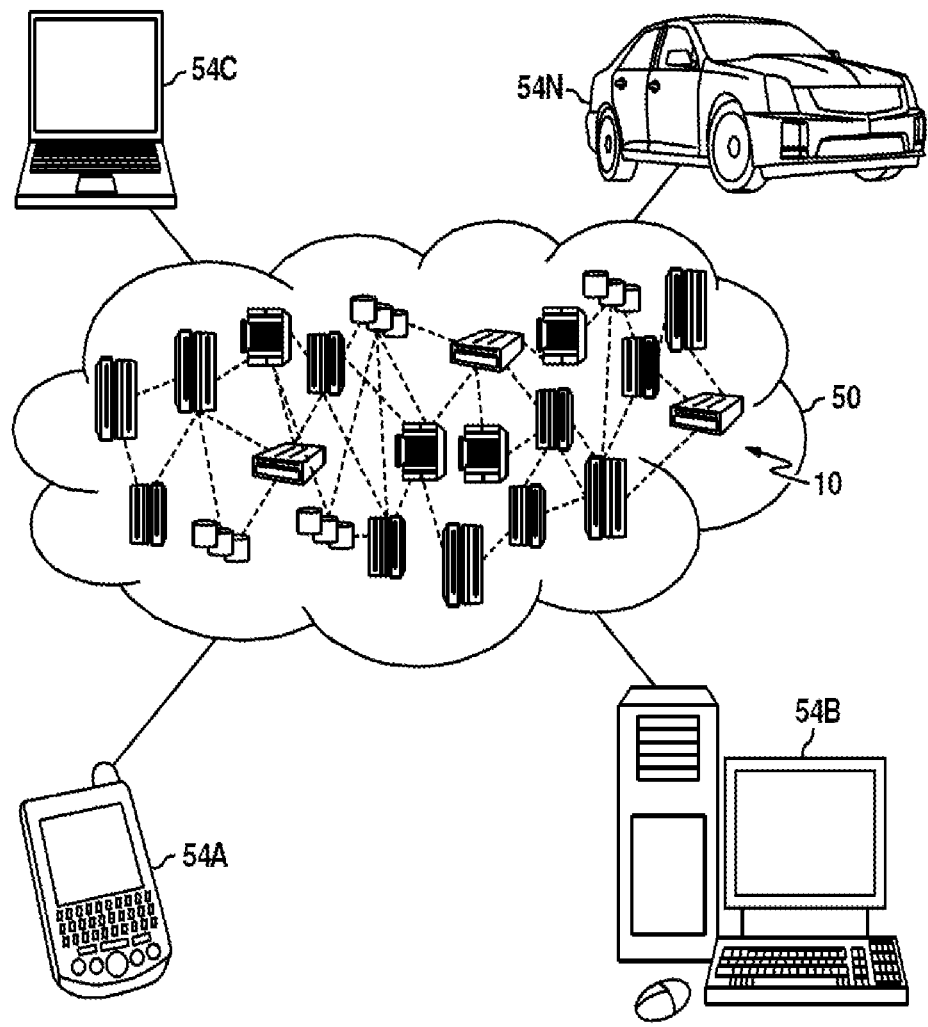
FIG. 9 depicts a cloud computing environment in accordance with one or more embodiments described herein.

Referring now to FIG. 9, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 9 are intended to be illustrative only and that computing nodes 10 and cloud computing environment 50 can communicate with any type of computerized device over any type of network and/or network addressable connection (e.g., using a web browser).

Figure 10:
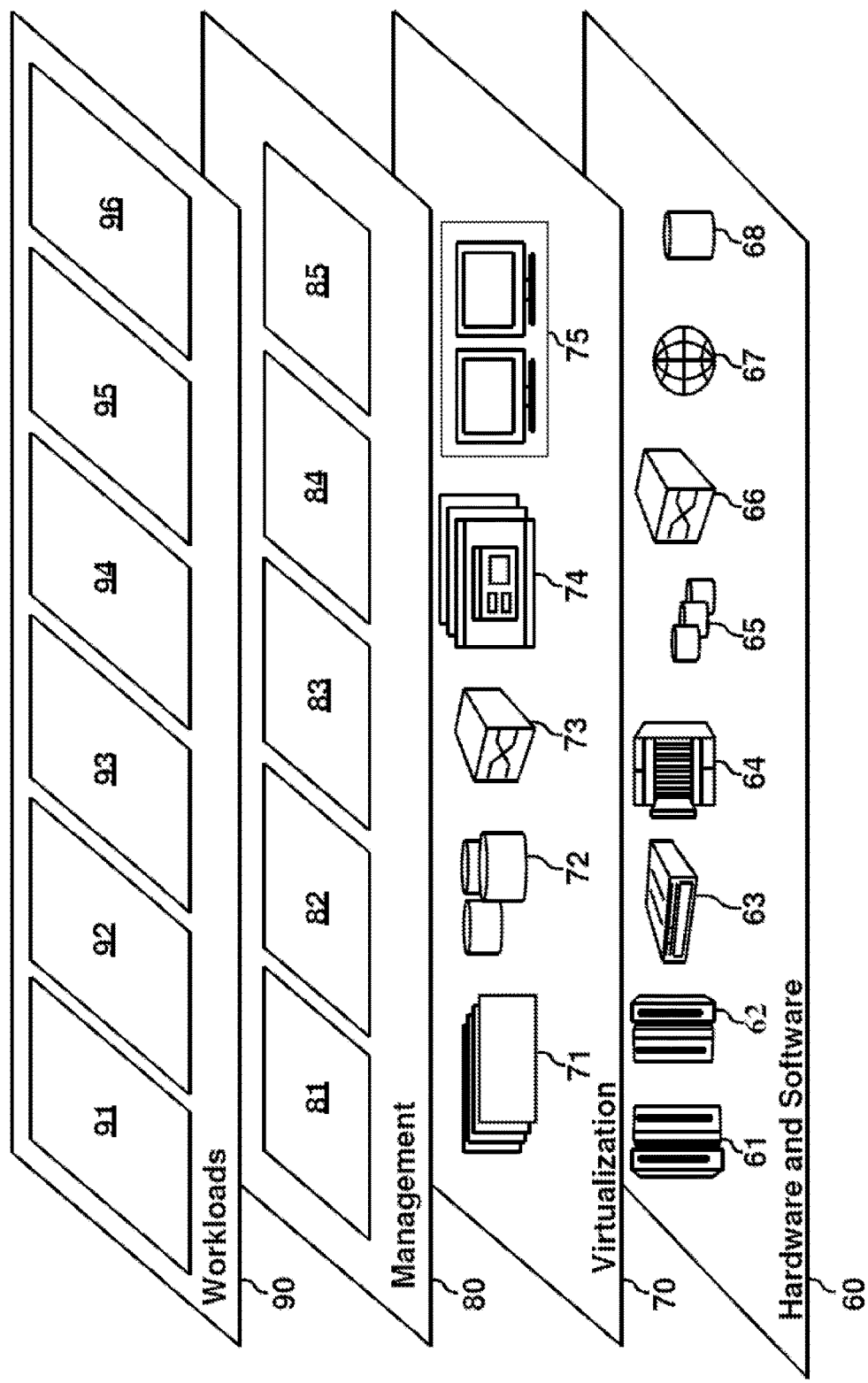
FIG. 10 depicts abstraction model layers in accordance with one or more embodiments described herein.

Referring now to FIG. 10, a set of functional abstraction layers provided by cloud computing environment 50 (FIG. 9) is shown. It should be understood in advance that the components, layers, and functions shown in FIG. 10 are intended to be illustrative only and embodiments of the invention are not limited thereto. As depicted, the following layers and corresponding functions are provided: Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, the procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and estimating node processing capacity values for order fulfillment 96.

The present invention can be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create method for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other method to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or non-volatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
    a memory that stores computer executable components; and
    a processor that executes the computer executable components stored in the memory, wherein the computer executable components comprise:
        a communication component that receives an input that defines a chemical compound, wherein the input specifies a constrained structure portion of a chemical compound that cannot be modified, and a first unconstrained structure portion of the chemical compound that can be modified; and
        an analysis component that determines a second unconstrained structure portion to replace the first unconstrained structure portion of the chemical compound based on a determination that the second unconstrained structure portion satisfies a defined condition related to a difference between the first unconstrained structure portion and the second unconstrained structure portion, and preserves a functional property of the chemical compound.

2. The system of claim 1, wherein the computer executable components further comprise a selection component that selects the second unconstrained structure portion from a molecule database that comprises one or more molecule patterns that can be utilized as the second unconstrained structure portion.

3. The system of claim 1, wherein the computer executable components further comprise a comparison component that compares a difference in one or more angles of one or more respective bonds between one or more atoms in the first unconstrained structure portion and one or more other atoms in the second unconstrained structure portion.

4. The system of claim 1, wherein the computer executable components further comprise a modification component that modifies a defined value of the defined condition based on another determination that an iteration failed to return the second unconstrained structure portion that satisfied the defined condition.

5. The system of claim 1, wherein the computer executable components further comprise a feedback component that returns the second unconstrained structure portion as an original unconstrained structure portion.

6. A computer program product for facilitating an iterative widening search for designing chemical compounds, the computer program product comprising a computer readable storage medium having program instructions embodied therewith, the program instructions executable by a processing component to cause the processing component to:
    receive an input that defines a first chemical compound, wherein the input specifies a constrained structure portion of a chemical compound that cannot be modified, and an unconstrained structure portion of the chemical compound that can be modified;

evaluate a data store that comprises one or more molecule patterns for a molecule pattern that can be substituted for the unconstrained structure portion of the first chemical compound and satisfies a defined condition related to a difference between the unconstrained structure portion and the molecule pattern, and preserves a functional property of the first chemical compound; and generate a second chemical compound that comprises the constrained structure portion and the molecule pattern substituted for the unconstrained structure portion.

7. The computer program product of claim 6, wherein the program instructions further cause the processing component to:

determine the difference in one or more angles of one or more respective bonds between one or more atoms in the unconstrained structure portion and one or more other atoms in the molecule pattern.

8. The computer program product of claim 6, wherein the program instructions further cause the processing component to:

perform an iteratively widening search based on the one or more molecule patterns, wherein the iteratively widening search is controlled by the defined condition.

9. The computer program product of claim 6, wherein the defined condition is a tolerance function selected based on the first chemical compound and the unconstrained structure portion.

\* \* \* \* \*